United States Patent [19]

Weaver et al.

[11] Patent Number: 5,091,501
[45] Date of Patent: Feb. 25, 1992

[54] PROCESS FOR PREPARING 2H-1-BENZOPYRAN-2-ONES AND POLYESTERS CONTAINING 2H-1-BENZOPYRAN-2-ONE RESIDUES

[75] Inventors: Max A. Weaver, Kingsport; Samuel D. Hilbert, Jonesborough; Wayne P. Pruett; Clarence A. Coates, Jr., both of Kingsport, all of Tenn.

[73] Assignee: Eastman Kodak Company, Rochester, N.Y.

[21] Appl. No.: 594,460

[22] Filed: Oct. 4, 1990

[51] Int. Cl.$^5$ .............................................. C08G 16/00
[52] U.S. Cl. .................................... 528/220; 528/272; 528/289; 528/290; 528/293; 528/295; 528/298; 528/302; 528/304; 528/308.6; 528/332; 528/335; 528/337; 528/377; 528/390; 528/391; 528/392; 528/401; 528/403; 525/411; 548/159; 548/223; 549/277; 549/280; 549/288
[58] Field of Search ............. 528/220, 272, 289, 290, 528/293, 295, 298, 302, 304, 308.6, 332, 335, 337, 377, 390, 391, 392, 401, 403; 525/411; 548/159, 223; 549/277, 280, 288

[56] References Cited

U.S. PATENT DOCUMENTS

| | | | |
|---|---|---|---|
| 3,148,163 | 9/1964 | Freyermuth | 524/110 |
| 3,285,993 | 11/1966 | Inamoto et al. | 528/305 |
| 4,105,665 | 8/1978 | Harnisch | 524/110 |
| 4,347,350 | 8/1982 | Horner et al. | 528/190 |
| 4,892,922 | 1/1990 | Weaver et al. | 528/190 |

OTHER PUBLICATIONS

Organic Reactions, Sethna & Phadke, 7, pp. 1, (1953).
Organic Reactions, J. R. Johnson, vol. 1, pp. 210, (1942).
Heterocyclic Compounds "Coumarins", R. C. Elderfield, vol. 2, p. 173.
Organic Syntheses, E. C. Horning et al, 1948, 28, p. 24.

*Primary Examiner*—Maurice J. Welsh
*Assistant Examiner*—Sam A. Acquah
*Attorney, Agent, or Firm*—Bernard J. Graves, Jr.; William P. Heath, Jr.

[57] ABSTRACT

This invention provides a process for producing 2H-1-benzopyran-2-ones (coumarins) from optionally-substituted o-halocinnamic acids or esters under polyester-forming conditions. When the coumarins contain appropriately reactive functional groups, and desired monomers are present, a colored or UV-absorbing coumarin/polyester copolymer is provided in one step.

8 Claims, No Drawings

PROCESS FOR PREPARING 2H-1-BENZOPYRAN-2-ONES AND POLYESTERS CONTAINING 2H-1-BENZOPYRAN-2-ONE RESIDUES

FIELD OF THE INVENTION

This invention belongs to the field of synthetic organic chemistry. More particularly, this invention provides a process for preparing 2H-1-benzopyran-2-ones (coumarins) under polyester-forming reaction conditions.

BACKGROUND OF THE INVENTION 2H-1-Benzopyran-2-ones (coumarins) can be prepared by the Peckman reaction ("The Peckman Reaction," S. Sethna and R. Phadke, *Organic Reactions* 1953, 7, 1), whereby optionally substituted phenols are condensed with malic acid or β-keto esters in the presence of a condensing agent such as sulfuric acid:

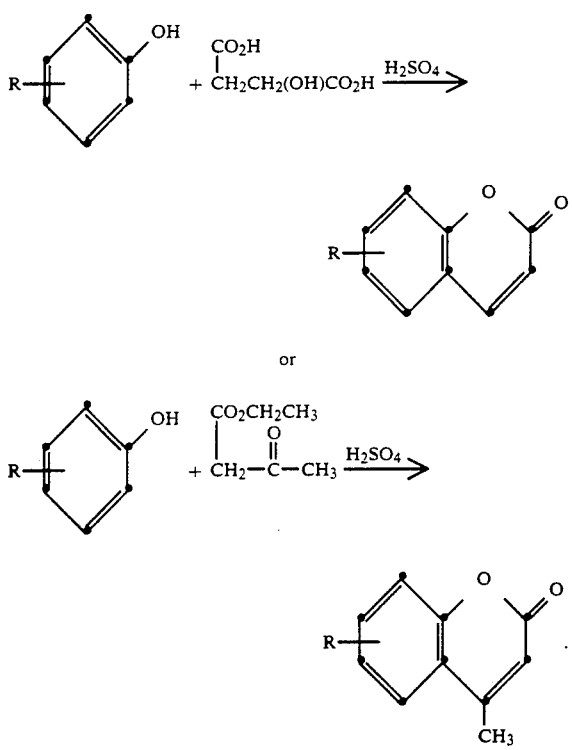

However, the Peckman reaction is often low-yielding and may provide undesired by-products which can only be removed with great difficulty.

Coumarins may also be prepared from optionally substituted salicylaldehydes by utilizing the Perkin reaction (Johnson, *Organic Reactions*, John Wiley and Sons, New York, 1942, Vol. 1, p. 210).

The Perkin reaction, however, is fraught with varying yields and formation of an undesired by-product as depicted.

Salicylaldehydes can also be reacted with esters of malonic acid to produce 3-substituted coumarins by application of the Knoevenagel reaction (Knoevenagel, Ber., 37, 4461 (1904); "Coumarins", *Heterocyclic Compounds*, Ed., R. C. Elderfield, Vol. 2, p. 173; E. C. Horning, et al., *Org. Synth.*, 1948, 28, p. 24; and "Coumarin and its Derivatives", *Chemistry of Carbon Compounds*, C. H. Rodd, Vol. IV B, p. 869).

Both the Perkin and Knoevenagel approaches suffer from the general unavailability and difficult synthesis of the necessary salicylaldehyde starting materials.

SUMMARY OF THE INVENTION

A novel process for preparing 2H-1-benzopyran-2-ones (coumarins) is provided. By the practice of the present invention, certain o-halocinnamic acids or esters are converted to the corresponding optionally substituted coumarin derivatives under conventional polyester forming conditions. The coumarins thus formed possess visible color and/or absorb light in the ultraviolet (UV) spectrum. When said coumarins possess a reactive group such as carboxy, alkoxycarbonyl, hydroxyl, etc., they may, under the same polyester forming conditions be incorporated within the polyester chain or become chain terminators to yield polymers particularly suitable for packaging materials where the desirability of colored or UV absorbing materials is sought without the drawback of extractability of the UV-screening or coloring agent.

DETAILED DESCRIPTION OF THE INVENTION

The present invention provides a process for preparing a compound of Formula (1)

(1)

wherein
$R_1$ is hydrogen, halo, $C_1-C_{10}$ alkyl, $C_1-C_{10}$ alkoxy, hydroxy, $C_1-C_{10}$ acyloxy, a group of the formula $-OR_2$ or $-N(R_2)(R_3)$,
wherein $R_2$ and $R_3$ are individually hydrogen; $C_3-C_8$ cycloalkyl optionally substituted with 1 or 2 groups selected from $C_1$-$C_{10}$ alkyl, hydroxy, $C_1$-$C_{10}$ acyloxy, $C_1$-$C_{10}$ alkoxy, halogen, or hydroxy $C_1$-$C_{10}$ alkyl; phenyl; substituted phenyl; $C_3$-$C_8$ alkenyl; $C_1$-$C_8$ alkyl; $C_1$-$C_8$ substituted alkyl; or $R_2$ and $R_3$ taken together with the nitrogen atom to which they are bonded form a pentamethylene, hexamethylene, ethylene oxyethylene, ethylene sulfonylethylene, ethylene thioethylene, or

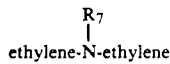
ethylene-N-ethylene wherein $R_7$ is hydrogen, $C_1$-$C_{10}$ alkyl, aryl, or a group of the formula —$XR_6$, wherein X is —CO—, —COO—, or —$SO_2$—, and $R_6$ is $C_1$-$C_{10}$ alkyl, or $C_1$-$C_{10}$ alkyl substituted with one or more halogen, hydroxy, phenoxy, aryl, cyano, $C_3$-$C_8$ cycloalkyl, $C_1$-$C_{10}$ alkylsulfonyl, $C_1$-$C_{10}$ alkanoyloxy, or $C_1$-$C_{10}$ alkoxy;

and Q is hydrogen; $C_1$-$C_{10}$ alkyl; $C_3$-$C_8$ cycloalkyl; benzyl; phenyl; substituted phenyl; cyano; formyl; $C_1$-$C_{10}$ alkoxycarbonyl; aryloxycarbonyl; $C_3$-$C_{10}$ carbalkenyloxy; $C_1$-$C_{10}$ acyl; aroyl; carboxy; carbamoyl; N-$C_1$-$C_{10}$ alkylcarbamoyl; N-arylcarbamoyl; N-$C_1$-$C_{10}$ alkyl-N-arylcarbamoyl; N-$C_3$-$C_8$ cycloalkylcarbamoyl; $C_1$-$C_{10}$ alkylsulfonyl; arylsulfonyl; or a heterocyclic aryl ring optionally substituted one or more times with $C_1$-$C_{10}$ alkyl, $C_1$-$C_{10}$ alkoxy, carboxy, $C_1$-$C_{10}$ alkoxycarbonyl, halogen, cyano, phenyl, or substituted phenyl; naphthyl; or naphthyl substituted by $C_1$-$C_{10}$ alkyl or halo;

which comprises subjecting a compound of Formula (2)

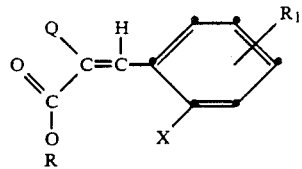
(2)

to polyester forming reaction conditions, wherein R is hydrogen, $C_1$-$C_{10}$ alkyl, $C_1$-$C_{10}$ substituted alkyl, substituted aryl, $C_3$-$C_{10}$ alkenyl, or $C_3$-$C_8$ cycloalkyl; x is chloro, bromo, fluoro, or iodo; and Q and $R_1$ are as defined above.

As a preferred aspect of the present invention, R is $C_1$-$C_{10}$ alkyl and one or both of $R_1$ and Q contain at least one carboxy, alkoxycarbonyl, aryloxycarbonyl, N-alkylcarbamoyloxy, $C_1$-$C_{10}$ acyloxy, chlorocarbonyl, carbamoyloxy, amino, $C_1$-$C_{10}$ alkylamino, hydroxy, N-phenylcarbamoyloxy, cyclohexanoyloxy, or carbocyclohexyloxy, wherein said alkyl and/or aryl groups are optionally substituted by hydroxy, cyano, $C_1$-$C_{10}$ acyloxy, $C_1$-$C_{10}$ alkoxycarbonyl, phenyl, phenoxy, hydroxy, $C_1$-$C_{10}$ alkyloxy, or halogen.

In this preferred aspect of the present invention, the process of the present invention is carried out in the presence of suitable diol and acidic monomeric starting materials as described below for preparing molding or fiber grade polyesters. The compositions thus provided have such colored or UV-absorbing coumarin chromophores copolymerized within the matrix. Thus, in one step, the desired coumarin may be formed, and if said coumarin contains one or more reactive functionalities as described above, it may be incorporated into a linear polyester matrix in the same reaction vessel concurrently.

The term "halo" as used herein refers to chloro, fluoro, iodo, and bromo.

The term "$C_1$-$C_{10}$ alkyl" refers to straight and branched alkyl groups. A preferred group within this group is the $C_1$-$C_4$ alkyl group.

The term "$C_1$-$C_{10}$ acyloxy" refers to a straight or branched alkyl chain (or hydrogen) attached to a carbonyloxy moiety. Examples of such groups include formyloxy, acetoxy, n-butanoyloxy, isopentanoyloxy, n-decanoyloxy, and the like.

The term "$C_1$-$C_{10}$ alkoxy" is used in its ordinary sense; i.e., examples of such groups include methoxy, n-butoxy, 2-ethylpentyloxy, n-octyloxy, n-decyloxy, and the like.

The term "substituted aryl" as used herein refers to an aryl ring substituted one or more times with halo, $C_1$-$C_{10}$ alkyl, $C_1$-$C_{10}$ substituted alkyl, $C_1$-$C_{10}$ acyloxy, $C_1$-$C_{10}$ alkoxy, $C_1$-$C_{10}$ alkoxycarbonyl, carboxy, or hydroxy. The term "substituted phenyl" refers to a phenyl ring substituted with such groups.

The term "$C_1$-$C_{10}$ substituted alkyl" refers to a $C_1$-$C_{10}$ straight or branched alkyl chain substituted once or twice with a group selected from halo, hydroxy, cyano, succinimido, hydroxysuccinimido, $C_1$-$C_{10}$ acyloxysuccinimido, glutarimido, phenylcarbamoyloxy, phthalimido, 4-carboxyphthalimido, phthalimidino, 2-pyrrolidino, cyclohexyl, phenyl, substituted phenyl, $C_1$-$C_{10}$ alkylsulfonyl, vinylsulfonyl, acrylamido, sulfamoyl, o-benzoic sulfimido, $C_1$-$C_{10}$ alkylsulfonamido, phenylsulfonylamino, $C_1$-$C_{10}$ alkoxycarbonylamino, $C_1$-$C_{10}$ alkylcarbamoyloxy, $C_1$-$C_{10}$ alkyloxycarbonyl, $C_1$-$C_{10}$ alkoxycarbonyloxy, $C_3$-$C_{10}$ alkenylcarbonylamino, a group of the formula

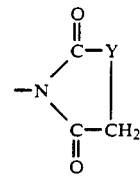

wherein
Y is —NH—, —N—$C_1$-$C_{10}$ alkyl, —O—, —S—, or —$CH_2O$—;
or a group of the formula —S—$R_4$ or —$SO_2CH_2CH_2SR_4$,
wherein $R_4$ is $C_1$-$C_{10}$ alkyl, phenyl substituted phenyl; pyridyl, pyrimidinyl, benzoxazolyl, benzimidazoloyl, benzothiazolyl, or a group of the formula

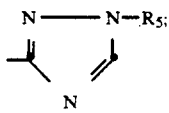

—O—A—$R_6$;
—$CONR_5R_6$; or
—$SO_2NR_5R_6$;
wherein $R_5$ is selected from hydrogen, aryl, $C_1$-$C_{10}$ alkyl, $C_1$-$C_{10}$ alkyl substituted once or twice with halo, hydroxy, phenoxy, aryl, cyano, $C_3$-$C_8$ cycloalkyl, $C_1$-$C_{10}$ alkylsulfonyl, $C_1$-$C_{10}$ alkylthio, $C_1$-$C_{10}$ alkanoyloxy, or $C_1$-$C_{10}$ alkoxy, and A is selected from —CO—, —COO—, or —$SO_2$— and $R_6$ is $R_5$ as defined herein and when A is —CO—, $R_6$ is amino, $C_3$-$C_{10}$ alkenyl, $C_1$-$C_{10}$ alkylamino, di($C_1$-$C_{10}$ alkyl)amino, arylamino, or furyl.

The term "aryl" as used herein refers to any aromatic carbocyclic ring. Examples of such rings include phenyl, naphthyl, phenanthryl, and the like.

The term "heterocyclic aryl ring" as used herein refers to a $C_2$-$C_8$ ring system containing one, two, or three hetero atoms selected from oxygen, sulfur, and nitrogen and which contains at least five members. Examples of such rings include furanyl, benzothienyl, 2-benzoxazolyl, 2-benzothiazolyl, 2-benzimidazolyl, 1,3,4-thiadiazol-2-yl, 1,2,4-thiadiazol-2-yl, 1,3,4-oxadiazol-2-yl, triazolyl, pyridyl, pyrrolyl, quinolyl, pyrimidinyl, thienyl, imidazolyl, and the like.

The starting materials of Formula (2), above, may be prepared from readily synthesized o-halo benzaldehydes and activated methylene groups as shown in the following scheme using the Knoevenagel reaction.

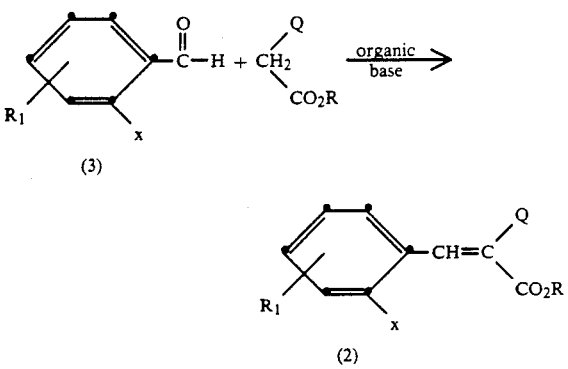

In the above reaction, suitable solvents are the polar aprotic and protic solvents, although the lower alcohols are preferred. It is also advantageous to utilize a solvent system which forms an azeotrope with water, e.g., benzene/toluene. In this fashion, the water produced in the above condensation may be removed as the reaction progresses, thus driving the reaction toward completion.

The aldehyde starting material of Formula (3) may be prepared by known methodology. For example, when $R_1$ is dialkylamino, the Vilsmeier reaction may be utilized [Bull. Society Chim de France, No. 10, 1989–99 (October, 1962); Angewandte Chemie, 72, No. 22, 836, 845, Nov. 21, 1960].

In the above formulae, x is preferably chloro or bromo.

As noted above, it is preferred that the product (1) of the above process possesses one or more "reactive groups", i.e., carboxy, alkoxycarbonyl, hydroxyl, etc. When such groups are present, it will be appreciated that the same reaction conditions utilized to form the coumarin compounds of Formula (1), will also, in the presence of desired monomeric starting material effect the polymerization of a polyester containing such colored or UV-absorbing coumarin compounds within the polymeric chain or become chain terminators. The polyesters thus formed are particularly useful as packaging material because exposure of the contents to ultraviolet radiation will be minimized while providing a UV screening agent or color which, since it is incorporated within the polymeric matrix, cannot be extracted from the polymer by its contents (e.g., liquid foodstuffs). In this regard, U.S. Pat. Nos. 4,882,412 and 4,892,922, Weaver et al., incorporated herein by reference, describe the utility of coumarins containing such reactive groups. It is thus a further aspect of the present invention, that the process of the present invention is carried out in the presence of desired monomeric starting materials to provide UV-absorbing polyester/coumarin copolymers.

The polyesters which may be used in the process herein include linear, thermoplastic, crystalline or amorphous polyesters produced by conventional polymerization techniques from one or more diols and one or more dicarboxylic acids. The polyesters normally are molding or fiber grade and have an inherent viscosity (I.V.) of about 0.4 to about 1.2.

Suitable diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, Z,8-bis(hydroxymethyl)-tricyclo-[5.2.1.0]-decane wherein Z represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms.

Suitable acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalenedicarboxylic acid and the like. In the polymer preparation, it is often preferable to use a functional acid derivative thereof such as the dimethyl, diethyl, or dipropyl ester of the dicarboxylic acid. The anhydrides or acid halides of these acids also may be employed where practical.

Preferred polyesters comprise at least about 50 mole percent terephthalic acid residues and at least about 50 mole percent ethylene glycol and/or 1,4-cyclohexanedimethanol residues. Particularly preferred polyesters are those containing from about 75 to 100 mole percent terephthalic acid residues and from about 75 to 100 mole percent ethylene glycol residues.

The linear polyesters may be prepared according to polyester forming conditions well known in the art. For example, a mixture of one or more dicarboxylic acids, preferably aromatic dicarboxylic acids, or ester forming derivatives thereof, and one or more diols may be heated in the presence of esterification and/or polyesterification catalysts at temperatures in the range of about 150° to about 300° C., and pressures of atmospheric to about 0.2 mm Hg. Normally, the dicarboxylic acid or derivative thereof is esterified or transesterified with the diol(s) at atmospheric pressure and at a temperature at the lower end of the specified range. Polycondensation then is effected by increasing the temperature and lowering the pressure while excess diol is removed from the mixture.

Typical catalyst or catalyst systems for polyester condensation are well-known in the art. For example, catalysts disclosed in U.S. Pat. Nos. 4,025,492; 4,136,089; 4,176,224; 4,238,593; and 4,208,527, incorporated herein by reference, are deemed suitable in this regard. Further, R. E. Wilfong, *Journal of Polymer Science*, 54 385 (1961) sets forth typical catalysts which are useful in polyester condensation reactions. A preferred catalyst system is that used in the experimental system below, namely Mn/Ti/Sb/Co/P.

A preferred temperature range for the process of the present invention is about 260° C. to about 300° C.

The polyester compositions provided by this process are useful in the manufacturing of containers or packages for comestibles such as beverages and food. By the use of known heat-setting techniques, certain of the polyesters are, in terms of color, I.V. and heat distortion, stable at temperatures up to about 100° C. Such stability characteristics are referred to herein as "hot-fill" stability. Articles molded from these polyesters exhibit good thin-wall rigidity, excellent clarity and good barrier properties with respect to moisture and atmospheric gases, particularly carbon dioxide and oxygen.

The linear polyesters most preferred for use in articles having "hot-fill" stability comprise poly(ethylene terephthalate), poly(ethylene terephthalate) wherein up to 5 mole percent of the ethylene glycol residues have been replaced with residues derived from 1,4-cyclohexanedimethanol and poly(ethylene 2,6-naphthalenedicarboxylate), wherein the polyesters have been sufficiently heat set and oriented by methods well known in the art to give a desired degree of crystallinity. By definition, a polymer is "hot-fill" stable at a prescribed temperature when less than 2% change in volume of a container manufactured therefrom occurs upon filling the same with a liquid at the temperature. For the manufacture of blow-molding beverage bottles, the most preferred polyesters have an I.V. of 0.65 to 0.85, and a Tg of >70° C., and film sections cut from the bottle have a Water Vapor Transmission Rate of 1.5 to 2.5 g mils/100 in.$^2$-24 hours, a Carbon Dioxide Permeability of 20 to 30 cc. mils/100 in.$^2$-24 hours-atm., and an Oxygen Permeability of 4 to 8 cc. mils/100 in.$^2$-24 hours-atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, Inc., of Elk River, Minn., and the Carbon Dioxide Permeability by the standard operating procedure of a MOCON PERMATRAN C II, also of Modern Controls.

The concentration of the residue of the benzopyran compound in the condensation polymer can be varied substantially depending, for example, on the depth of shade or color desired and/or the end use for which the polyester composition is intended. When the colored composition is to be used in the fabrication of relatively thin-walled containers, the concentration of the residue of the benzopyran compound normally will be in the range of about 50 to 1500 ppm (parts by weight per million parts by weight polymer) with the range of about 200 to 800 ppm being especially preferred.

The invention will now be described in greater detail by reference to the following examples.

EXPERIMENTAL SECTION

Example 1

Preparation of 7-(Diethylamino)-2-oxo-2H-1-benzopyran-3-carbonitrile

A mixture of 4-diethylaminosalicyladehyde (1.93 g, 0.01 m), ethyl cyanoacetate (1.13 g, 0.01 m), ethanol (15 mL), and piperidine (10 drops) is heated at reflux for 5 hrs. and allowed to cool. The product crystallizes and is collected by filtration, washed with ethanol and dried in air. By mass spectroscopy the product was determined to have the following structure:

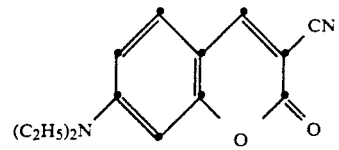

Example 2

Preparation of Ethyl 3-[2-Chloro-4-(diethylamino)phenyl]-2-cyano-2-propenoate

A mixture of 2-chloro-4(diethylamino)benzaldehyde (10.55 g, 0.05 m), ethyl cyanoacetate (5.65 g, 0.05 m), piperidine (2 drops), acetic acid (2 drops), and ethanol (25 mL) is heated at reflux for 1.5 hr and allowed to cool. The crystallized product is collected by filtration, washed with ethanol and dried in air. A yield of 13.6 g of product, 89% of the theoretical yield, is obtained. Mass spectrometry supports the following structure:

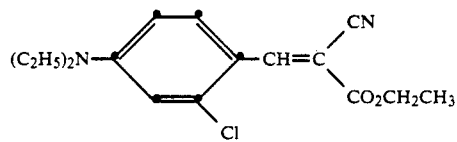

Example 3

Preparation of Poly(ethylene terephthalate) with 5 wt % Ethyl 3-[2-chloro-4-diethylamino phenyl]-2-cyano-2-propenoate The following compounds are placed in a 500 mL, single-necked round-bottom flask 97 g (0.5 mol) dimethyl terephthalate 62 g (1.0 mole) ethylene glycol 5.1 g (5%) ethyl 3-[2-chloro-4-(diethylamino)phenyl]-2-cyano-2-propenoate (from Example 2)

1.1 mL of an ethylene glycol solution of Mn(OCOCH$_3$)$_2$.4H$_2$O which contains 0.0053 g Mn 0.064 mL of a n-butanol solution of acetyltriisopropyl titanate which contains 0.00192 g Ti 0.0345 g Sb$_2$O$_3$ 0.64 mL of an ethylene glycol solution of Co(OCOCH$_3$).4H$_2$O which contains 0.0072 g Co The flask is equipped with a nitrogen inlet, stirrer, vacuum outlet, and condensing flask. The flask and contents are heated at 200° C. in a Belmont metal bath for 60 min and at 210° C. for 75 min with a nitrogen sweep over the reaction mixture. Then 1.57 mL of an ethylene glycol slurry of Zonyl A which contains 0.012 g phosphorus is added. The temperature of the bath is increased to 230° C. At 230° C., a vacuum with a slow stream of nitrogen bleeding in the system is applied over a 5 min period until the pressure is reduced to 200 mm Hg. The flask and contents are heated at 230° C. under a pressure of 200 mm Hg for 25 min. The metal bath temperature is increased to 270° C. At 270° C., the pressure is reduced slowly to 100 mm Hg. The flask and contents are heated at 270° C. under a pressure of 100 mm Hg for 30 min. The metal bath temperature is increased to 285° C. and the pressure is reduced slowly to 4.5 mm Hg. The flask and contents are heated at 285° C. under a pressure of 4.5 mm Hg for 25 min. The pressure is reduced to 0.3 mm Hg and polycondensation is continued for 40 min. The flask is removed from the bath and is allowed to cool in nitrogen atmosphere while the polymer solidifies. The resulting polymer is ground to pass a 2 mm screen. The resulting yellow polymer has an inherent viscosity of 0.38 measured in a 60/40 ratio by weight of phenol/tetrachloroethane at a concentration of 0.5 g per 100 mL.

Example 4

Extraction of 7-(Diethylamino)-2-oxo-2H-1-benzopyran-3-carbonitrile from Polymer A portion of the yellow polymer (30.0 g) prepared in Example 3 is placed in thimble of Soxhlet extractor and extracted with 1 liter of acetone for 4 hr. The colorant is recovered from the acetone by removing the acetone under vacuum. The solid residue is stirred with a little methanol and filtered. Thin-layer chromatography is used to compare the product to the compound of Examples 1 and 2. The Rf values of the product and the compound of Example 1 are identical. Also, mass spectrometry shows that the molecular ions are identical. Thus, it is concluded that ring closure occurred to form the coumarin ring as follows:

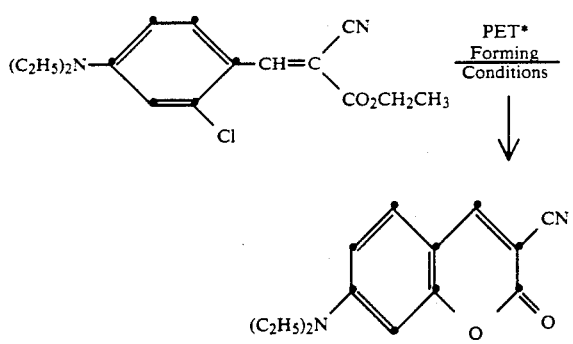

PET* = polyethylene terephthalate

The product is also fluorescent, which is characteristic of coumarin compounds.

Example 5

Preparation of Diethyl [[2-chloro-4-(1,1-dioxo-4-thiomorpholinyl)phenyl]methylene]propanedioate A mixture of 2-chloro-4-(1,1-dioxy-4-thiomorpholinyl)-benzaldehyde (1.15 g, 0.004 m), diethyl malonate (0.64 g, 0.004 m), ethanol (20 mL), and piperidine (2 drops) is heated at reflux for 12 hr. Upon cooling and standing overnight the product crystallizes and is collected by filtration, washed with a little ethanol, and dried in air. A yield of 1.0 g, 60% of the theoretical is obtained. The product has the following structure as confirmed by mass spectrometry:

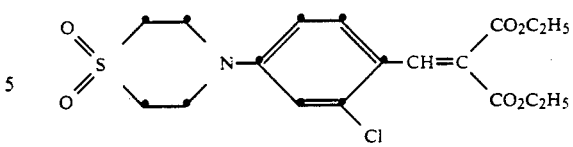

In methylene chloride, an absorption maximum ($\lambda$ max) is observed at 337 nm.

Example 6

Preparation of Poly(ethylene terephthalate) Containing Ring-Closed Product Obtained from Product of Example 5

The following compounds are placed in a 500-mL, three-necked, round-bottom flask:
97 g (0.5 mol) dimethyl terephthalate
62 g (1.0 mol) ethylene glycol
0.064 mL of a n-butanol solution of acetyltriisopropyl titanate which contains 0.00192 g Ti
1.1 mL of an ethylene glycol solution of Mn(O-COCH$_3$)$_2$.4H$_2$O which contains 0.0053 g Mn
0.00345 g Sb$_2$O$_3$
0.64 mL of an ethylene glycol solution of Co(O-COCH$_3$)$_2$.4H$_2$O which contains 0.0072 g Co The flask is equipped with a nitrogen inlet, stirrer, vacuum outlet, and condensing flask. The flask and contents are heated at 200° C. in a Belmont metal bath for 60 min and at 210° C. for 75 min with a nitrogen sweep over the reaction mixture. Then 1.57 mL of an ethylene glycol slurry of Zonyl A which contains 0.012 g phosphorus is added. The temperature of the bath is increased to 230° C. At 230° C., 0.0384 g diethyl[[2-chloro-4-(1,1-dioxo-4-thiomorpholinyl) phenyl]methylene]propanedioate (product from Example 5) is added to the flask. Five minutes after this addition, a vacuum with a slow stream of nitrogen bleeding in the system is applied over a five-minute period until the pressure is reduced to 200 mm Hg. The flask and contents are heated at 230° C. under a pressure of 200 mm Hg for 25 min. The metal bath temperature is increased to 270° C. At 270° C. the pressure is reduced slowly to 100 mm Hg. The flask and contents are heated at 270° C. under a pressure of 100 mm Hg for 30 min. The metal bath temperature is increased to 285° C. and the pressure is reduced slowly to 4.5 mm Hg. The flask and contents are heated at 285° C. under a pressure of 4.5 mm Hg for 25 min. Then the pressure is reduced to 0.25 mm Hg and polycondensation is continued for 40 min. The flask is removed from the metal bath and is allowed to cool in nitrogen atmosphere while the polymer crystallizes. The resulting polymer has an inherent viscosity of 0.54 measured in a 60/40 ratio by weight of phenol/tetrachloroethane at a concentration of 0.5 g per 100 mL. An amorphous 14.5 mil thick film molded from this polymer to simulate the sidewall of a container shows a strong absorption peak at 383 nm.

The polymer has a high degree of blue-white fluorescence and UV absorbing properties which indicate formation of the following structure:

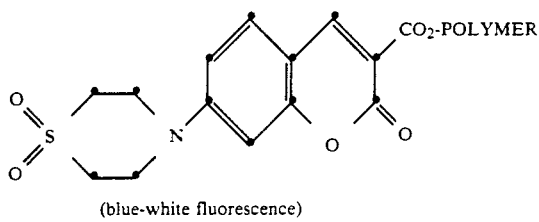

(blue-white fluorescence)

Example 7

Preparation of Diethyl[[2-chloro-4(di-2-chloroethylamino)phenyl]methylene]propanedioate A mixture of 2-chloro-4-(di-2-chloroethylamino) benzaldehyde (1.40 g, 0.005 m), diethyl malonate (0.80 g), ethanol (15 mL), piperidine (2 drops), and acetic acid (2 drops) is heated at reflux for 8 hr. Ethanol is stripped from the reaction mixture under vacuum to yield an oily product, which has the following structure by mass spectrometry:

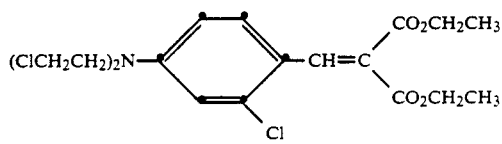

$\lambda$ max = 339 nm ($CH_2Cl_2$)

Example 8

Preparation of Poly(ethylene terephthalate) Containing Rinq-Closed Product From Diethyl[[2-chloro-4-(di-2-chloroethylamino)phenyl]-methylene]propanedioate The following compounds are placed in a 500-mL, three-necked, round-bottom flask:
97 g (0.5 mol) dimethyl terephthalate
62 g (1.0 mol) ethylene glycol
0.064 mL of a n-butanol solution of acetyltriisopropyl titanate which contains 0.00192 g Ti
1.1 mL of an ethylene glycol solution of Mn(O-COCH$_3$)$_2$.4H$_2$O which contains 0.0053 g Mn
0.0345 g Sb$_2$O$_3$
0.64 mL of an ethylene glycol solution of Co(O-COCH$_3$)$_2$.4H$_2$O which contains 0.0072 g Co The flask is equipped with a nitrogen inlet, stirrer, vacuum outlet, and condensing flask. The flask and contents are heated at 200° C. in a Belmont metal bath for 60 min and at 210° C. for 75 min with a nitrogen sweep over the reaction mixture. Then 1.57 mL of an ethylene glycol slurry of Zonyl A ™ which contains 0.012 g phosphorus is added. The temperature of the bath is increased to 230° C. At 230° C., 0.0384 g diethyl[[2-chloro-4-(di-2-chloroethylamino)phenyl]methylene]propanedioate are added to the flask. Five minutes after this addition, a vacuum with a slow stream of nitrogen bleeding in the system is applied over a five-minute period until the pressure is reduced to 200 mm Hg. The flask and contents are heated at 230° C. under a pressure of 200 mm Hg for 25 min. The metal bath temperature is increased to 270° C. At 270° C. the pressure is reduced slowly to 100 mm Hg. The flask and contents are heated at 270° C. under a pressure of 100 mm Hg for 30 min. The metal bath temperature is increased to 285° C. and the pressure is reduced slowly to 4.5 mm Hg. The flask and contents are heated at 285° C. under a pressure of 4.5 mm Hg for 25 min. Then the pressure is reduced to 0.25 mm Hg and polycondensation is continued for 40 min. The flask is removed from the metal bath and is allowed to cool in nitrogen atmosphere while the polymer crystallizes. The resulting polymer has an inherent viscosity of 0.52 measured in a 60/40 ratio by weight of phenol/tetrachloroethane at a concentration of 0.5 g per 100 mL. An amorphous 14.5 mil thick film molded from this polymer to simulate the sidewall of a container shows a strong absorption peak at 405 nm and is highly fluorescent which indicates formation of the coumarin compound.

Examples 9 through 60 below further illustrate compounds of Formula (2), above, which can be converted to the corresponding coumarin by practice of the process of the present invention.

o-Halocinnamic Acids and Esters

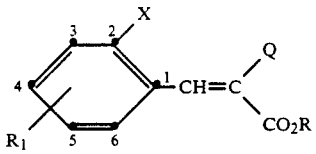

| EXAMPLE NO. | R | R$_1$ | X | Q |
|---|---|---|---|---|
| 9 | —CH$_3$ | 4-N(C$_2$H$_4$CO$_2$CH$_3$)$_2$ | Cl | CN |
| 10 | —C$_2$H$_5$ | 4-N(C$_2$H$_4$CO$_2$C$_2$H$_5$)$_2$ | Cl | —CO$_2$C$_2$H$_5$ |
| 11 | —CH$_3$ | 4-N(CH$_3$)C$_2$H$_4$CO$_2$CH$_3$ | Cl | —CO$_2$CH$_3$ |
| 12 | H | 4-N(C$_6$H$_{11}$)C$_2$H$_4$OCCH$_3$ (O) | Br | —CO$_2$CH$_3$ |
| 13 | —CH$_2$CH$_2$OH | 4-N(C$_2$H$_4$CO$_2$H)$_2$ | Br | H |
| 14 | —CH$_2$CH$_2$OCH$_3$ | 4-N(C$_6$H$_5$)C$_2$H$_4$OCCH$_3$ (O) | Br | —C$_6$H$_4$-p-CN |
| 15 | n-C$_4$H$_9$ | 4-N(C$_2$H$_4$OH)$_2$ | Cl | CN |

-continued o-Halocinnamic Acids and Esters

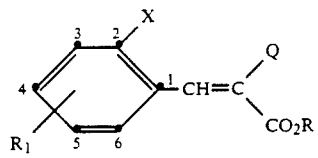

| EXAMPLE NO. | R | $R_1$ | X | Q |
|---|---|---|---|---|
| 16 | $-CH_2CH_2Cl$ | $4-N(C_2H_4OH)_2$ | I | $-CONHC_6H_5$ |
| 17 | $-CH_2CH_2OCH_2CH_2OH$ | $4-N(C_2H_4OH)_2$ | F | $-SO_2C_6H_5$ |
| 18 | $-CH_2C_6H_5$ | 4-OH | Cl | CN |
| 19 | $-CH_2CH_2OC_6H_5$ | $4-OCH_3$ | Cl | $-CO_2C_2H_5$ |
| 20 | $-CH_2C_6H_{11}$ | $4-OC_2H_4OH$ | Cl | CN |
| 21 | $-C_6H_5$ | $4-OCH_2CO_2C_2H_5$ | Br | $-SO_2C_6H_5$ |
| 22 | $-CH_2CH_2CN$ | $4-OC_2H_4OCCH_3$ (O) | Cl | $-COC_6H_5$ |
| 23 | $-CH_3$ | H | Br | $-CO_2C_2H_5$ |
| 24 | $-CH_3$ | 3-Cl | Cl | $-CO_2C_2H_5$ |
| 25 | $-CH_3$ | $3-Cl-4-N(CH_3)_2$ | Cl | $-CO_2C_2H_5$ |
| 26 | $-C_2H_5$ | $4-N(C_2H_4OH)_2$ | Cl | benzoxazole |
| 27 | $-C_2H_5$ | $4-N(C_2H_4OCCH_3)_2$ (O) | Cl | benzothiazole |
| 28 | $-C_2H_5$ | $4-N(C_2H_4OCCH_3)_2$ (O) | Cl | benzimidazole |
| 29 | $-C_2H_5$ | $4-N(C_2H_4OCOC_2H_5)_2$ (O) | Cl | pyridine |
| 30 | $-C_2H_5$ | $4-N(C_2H_4OCC_6H_5)_2$ (O) | Cl | thiophene |
| 31 | $-C_2H_5$ | $4-N(C_2H_4OC\text{-cyclohexyl})_2$ (O) | Cl | pyrrole |

-continued o-Halocinnamic Acids and Esters

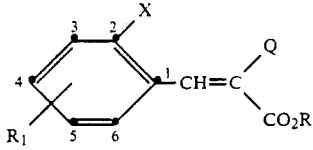

| EXAMPLE NO. | R | $R_1$ | X | Q |
|---|---|---|---|---|
| 32 | —$CH_3$ | 4-N($C_2H_4$O$\overset{O}{\overset{\|}{C}}$$CH_2OCH_3$)$_2$ | Cl | 1H-1,2,4-triazol-3,5-diyl |
| 33 | —CH($CH_3$)$_2$ | 4-N($C_2H_4OC_2H_4OH$)$_2$ | Cl | 2,4-dimethylthiazol-type group |
| 34 | —$CH_2CH(CH_3)_2$ | 4-N($CH_3$)$CH_2$(OH)$CH_2OH$ | Cl | —$CO_2CH_2CH_2OH$ |
| 35 | —$CH_3$ | 4-N($C_2H_4CN$)$C_2H_4OH$ | Cl | N-methyl-N-(propen-2-yl)benzamide group |
| 36 | —$CH_3$ | 3-$OCH_3$-4-N($C_2H_5$)$_2$ | Cl | —$CO_2C_2H_5$ |
| 37 | —$CH_3$ | 3-$CH_3$-4-N($CH_3$)$_2$ | Cl | —$SO_2CH_3$ |
| 38 | —$CH_3$ | 4-N($C_2H_5$)$_2$ | Cl | methyl 4-(prop-2-ylideneamino)-3-oxo-benzoate group |
| 39 | —$CH_3$ | 4-N($CH_2C_6H_4p$-$CO_2CH_3$)$_2$ | Br | CN |
| 40 | —$C_2H_5$ | 4-N($CH_2C_6H_5$)$_2$ | Br | —$CO_2C_2H_5$ |
| 41 | —$C_2H_5$ | 4-N($C_6H_5$)$_2$ | Br | CN |
| 42 | —$CH_2$-furan-2-yl | 4-N($C_2H_4OCH_3$)$_2$ | Br | methyl furan-2-carboxylate-yl |
| 43 | —$CH_2$-(5-hydroxymethyl-thiophen-2-yl) | 4-N($C_2H_5$)$C_2H_4$N(COCH$_2$)(COCH$_2$) | Br | —CONH—$C_6H_4$—$CO_2CH_3$ |
| 44 | —$C_2H_5$ | 4-N(n-$C_4H_9$)$_2$ | Cl | —$CO_2C_2H_5$ |
| 45 | —$C_2H_5$ | 4-O$CH_2$—$C_6H_4$—$CO_2CH_3$ | Cl | —$SO_2$—(2,5-dichlorophenyl) |
| 46 | —$C_2H_5$ | 4-O—$C_6H_4$—$CO_2CH_3$ | Cl | —COC($CH_3$)$_3$ |

-continued o-Halocinnamic Acids and Esters

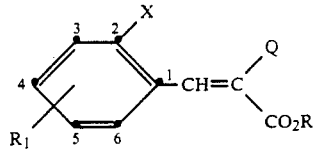

| EXAMPLE NO. | R | R₁ | X | Q |
|---|---|---|---|---|
| 47 | $-C_2H_5$ | 3,5-di-$CH_3$-4-$OCH_2CH_2OH$ | Br | (N=N isoxazole ring) |
| 48 | $-C_2H_5$ | 4-$N(C_2H_5)C_2H_4CO_2C_2H_5$ | Br | –C₆H₄–$CO_2CH_3$ |
| 49 | $-C_2H_5$ | 4-$C_2H_5$ | Br | $-CONHC_2H_4OH$ |
| 50 | $-C_2H_5$ | 4-$N(CH_3)_2$ | Br | $-CONH$–C₆H₄–$C_2H_4OH$ |
| 51 | $-C_2H_5$ | 4-$N(C_2H_5)C_2H_4CN$ | Br | $-CO_2C_2H_5$ |
| 52 | $-C_2H_5$ | 4-$N[CH_2CH(OH)CH_3]_2$ | Br | (thiophene)–$CO_2CH_3$ |
| 53 | $-C_2H_5$ | 4-$N(C_2H_4SCH_3)_2$ | Br | (naphthyl) |
| 54 | $-C_2H_5$ | 4-$OCCH_3$ (O=) | Br | $-CO_2C_2H_5$ |
| 55 | $-C_2H_5$ | 4-$N(C_2H_4O$–C₆H₄–$CO_2CH_3)_2$ | Br | CN |
| 56 | $-CH_2$–(thiophene)–$CH_2OH$ | 4-$N(C_2H_5)CH_2CH_2CONH_2$ | Br | $-CO_2CH_2$–(thiophene)–$CH_2OH$ |
| 57 | $-C_2H_5$ | 4-$N(CH_2CH_2SO_2C_6H_5)_2$ | Br | $-CO_2C_2H_5$ |
| 58 | $-C_2H_5$ | 4-N(...$SO_2$) thiomorpholine dioxide | Br | $-CO_2C_2H_5$ |
| 59 | $-C_2H_5$ | 4-N(...O) morpholino | Cl | $-CO_2C_2H_5$ |

| o-Halocinnamic Acids and Esters |
|---|

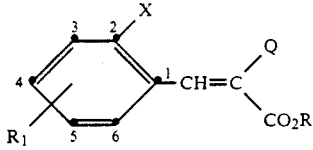

| EXAMPLE NO. | R | $R_1$ | X | Q |
|---|---|---|---|---|
| 60 | $-C_2H_5$ | $4-N(CH_2CH=CH_2)_2$ | Br | $-CO_2C_2H_5$ |

We claim:

1. A process for preparing a compound of Formula (1)

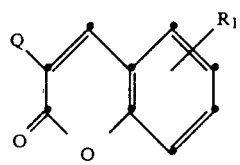

wherein
$R_1$ is hydrogen, halo, $C_1-C_{10}$ alkyl, $C_1-C_{10}$ alkoxy, hydroxy, $C_1-C_{10}$ acyloxy, a group of the formula $-OR_2$ or $-N(R_2)(R_3)$, wherein $R_2$ and $R_3$ are individually hydrogen; $C_3-C_8$ cycloalkyl optionally substituted with 1 or 2 groups selected from $C_1-C_{10}$ alkyl, hydroxy, $C_1-C_{10}$ acyloxy, $C_1-C_{10}$ alkoxy, halogen, or hydroxy $C_1-C_{10}$ alkyl; phenyl; substituted phenyl; $C_3-C_8$ alkenyl; $C_1-C_8$ alkyl; $C_1-C_8$ substituted alkyl; or $R_2$ and $R_3$ taken together with the nitrogen atom to which they are bonded form a pentamethylene, hexamethylene, ethylene oxyethylene, ethylene sulfonylethylene, ethylene thioethylene, or

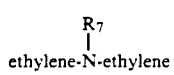

wherein $R_7$ is hydrogen, $C_1-C_{10}$ alkyl, aryl, or a group of the formula $-XR_6$, wherein X is $-CO-$, $-COO-$, or $-SO_2-$, and $R_6$ is $C_1-C_{10}$ alkyl, or $C_1-C_{10}$ alkyl substituted with one or more halogen, hydroxy, phenoxy, aryl, cyano, $C_3-C_8$ cycloalkyl, $C_1-C_{10}$ alkylsulfonyl, $C_1-C_{10}$ alkanoyloxy, or $C_1-C_{10}$ alkoxy;

and Q is hydrogen; $C_1-C_{10}$ alkyl; $C_3-C_8$ cycloalkyl; benzyl; phenyl; substituted phenyl; cyano; formyl; $C_1-C_{10}$ alkoxycarbonyl; aryloxycarbonyl; $C_3-C_8$ alkenyloxycarbonyl; $C_1-C_{10}$ acyl; aroyl; carboxy; carbamoyl; N-$C_1-C_{10}$ alkylcarbamoyl; N-arylcarbamoyl; N-$C_1-C_{10}$ alkyl-N-arylcarbamoyl; N-$C_3-C_8$ cycloalkylcarbamoyl; $C_1-C_{10}$ alkylsulfonyl; arylsulfonyl; or a heterocyclic aryl ring optionally substituted one or more times with $C_1-C_{10}$ alkyl, $C_1-C_{10}$ alkoxy, carboxy, $C_1-C_{10}$ alkoxycarbonyl, halogen, cyano, aryl, or substituted phenyl; naphthyl; or naphthyl substituted by $C_1-C_{10}$ alkyl or halo;

which comprises subjecting a compound of Formula (2)

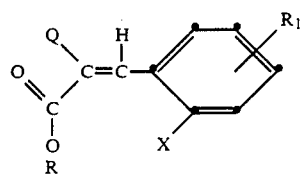

to polyester forming reaction conditions, wherein R is hydrogen, $C_1-C_{10}$ alkyl, $C_1-C_{10}$ substituted alkyl, substituted aryl, $C_3-C_{10}$ alkenyl, or $C_3-C_8$ cycloalkyl; x is chloro, bromo, fluoro, or iodo; and Q and $R_1$ are as defined above.

2. The process of claim 1 wherein R is $C_1-C_{10}$ alkyl and one or both of $R_1$ and Q contain at least one carboxy, $C_1-C_{10}$ alkoxycarbonyl, aryloxycarbonyl, N-$C_1-C_{10}$ alkylcarbamoyloxy, $C_1-C_{10}$ acyloxy, chlorocarbonyl, carbamoyloxy, amino, $C_1-C_{10}$ alkylamino, hydroxy, N-phenylcarbamoyloxy, cyclohexanoyloxy, or carbocyclohexyloxy, wherein said alkyl and/or aryl groups are optionally substituted by hydroxy, cyano, $C_1-C_{10}$ acyloxy, $C_1-C_{10}$ alkoxycarbonyl, phenyl, phenoxy, hydroxy, $C_1-C_{10}$ alkyloxy, or halogen.

3. A process for preparing a composition comprising molding grade polyester having copolymerized therein or reacted therewith the residue of a compound of Formula (1)

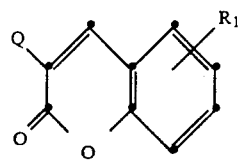

wherein
$R_1$ is hydrogen, halo, $C_1-C_{10}$ alkyl, $C_1-C_{10}$ alkoxy, hydroxy, $C_1-C_{10}$ acyloxy, a group of the formula $-OR_2$ or $-N(R_2)(R_3)$, wherein $R_2$ and $R_3$ are individually hydrogen; $C_3-C_8$ cycloalkyl optionally substituted with 1 or 2 groups selected from $C_1-C_{10}$ alkyl, hydroxy, $C_1-C_{10}$ acyloxy, $C_1-C_{10}$ alkoxy, halogen, or hydroxy $C_1-C_{10}$ alkyl; phenyl; substituted phenyl; $C_3-C_8$ alkenyl; $C_1-C_8$ alkyl; $C_1-C_8$ substituted alkyl; or $R_2$ and $R_3$ taken together with the nitrogen atom to which they are bonded form a pentamethylene, hexamethylene, ethylene oxyethylene, ethylene sulfonylethylene, ethylene thioethylene, or

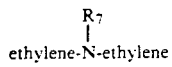

wherein $R_7$ is hydrogen, $C_1$–$C_{10}$ alkyl, aryl, or a group of the formula —$XR_6$, wherein X is —CO—, —COO—, or —SO$_2$—, and $R_6$ is $C_1$–$C_{10}$ alkyl, or $C_1$–$C_{10}$ alkyl substituted with one or more halogen, hydroxy, phenoxy, aryl, cyano, $C_3$–$C_8$ cycloalkyl, $C_1$–$C_{10}$ alkylsulfonyl, $C_1$–$C_{10}$ alkanoyloxy, or $C_1$–$C_{10}$ alkoxy;

and Q is hydrogen; $C_1$–$C_{10}$ alkyl; $C_3$–$C_8$ cycloalkyl; benzyl; phenyl; substituted phenyl; cyano; formyl; $C_1$–$C_{10}$ alkoxycarbonyl; aryloxycarbonyl; $C_3$–$C_8$ alkenyloxycarbonyl; $C_1$–$C_{10}$ acyl; aroyl; carboxy; carbamoyl; N-$C_1$–$C_{10}$ alkylcarbamoyl; N-$C_1$–$C_{10}$ alkyl-N-arylcarbamoyl; N-$C_3$–$C_8$ cycloalkylcarbamoyl; $C_1$–$C_{10}$ alkylsulfonyl; arylsulfonyl; or a heterocyclic aryl ring optionally substituted one or more times with $C_1$–$C_{10}$ alkyl, $C_1$–$C_{10}$ alkoxy, carboxy, $C_1$–$C_{10}$ alkoxycarbonyl, halogen, cyano, phenyl, or substituted phenyl; naphthyl; or naphthyl substituted by $C_1$–$C_{10}$ alkyl or halo;

provided that the compound of Formula (1) bears at least one substituent that is reactive with one of the monomers from which the polyester is derived, which comprises subjecting a compound of Formula (2)

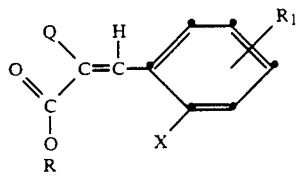

to polyester forming conditions, wherein R is hydrogen, $C_1$–$C_{10}$ alkyl, $C_1$–$C_{10}$ substituted alkyl, substituted aryl, $C_3$–$C_{10}$ alkenyl, or $C_3$–$C_8$ cycloalkyl; x is chloro, bromo, fluoro, or iodo; and Q and $R_1$ are as defined above;

in the presence of suitable diols and diacids.

4. The process of claim 3 wherein the suitable diol(s) is (are) selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, Z,8-bis(hydroxymethyl)-tricyclo-[5.2.1.0]-decane wherein Z represents 3, 4, or 5; diethylene glycol, triethylene glycol, dipropylene glycol, and tripropylene glycol;

and the suitable acid(s) is (are) selected from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, and 2,6-naphthalenedicarboxylic acid.

5. The process of claim 4 wherein the process is carried out in the presence of at least about 50 mole percent of terephthalic acid and at least about 50 mole percent of ethylene glycol and/or 1,4-cyclohexanedimethanol.

6. The process of claim 4 wherein the reaction is carried out in the presence of about 75 to about 100 mole percent of terephthalic acid to about 75 to about 100 mole percent of ethylene glycol.

7. The process of claim 1 wherein R is $C_1$–$C_4$ alkyl, $R_1$ is —$OR_2$ or —$N(R_2)R_3$ and is in the 6-position; Q is phenyl, cyano, $C_1$–$C_4$ alkoxycarbonyl, $C_1$–$C_4$ alkanoyl, benzoyl, carbamoyl, N-$C_1$–$C_4$ alkylcarbamoyl, N-phenylcarbamoyl, $C_1$–$C_4$ alkylsulfonyl, phenylsulfonyl, or a heterocyclic aryl ring optionally substituted one or more times with $C_1$–$C_4$ alkyl, $C_1$–$C_4$ alkoxy, carboxy, $C_1$–$C_4$ alkoxycarbonyl, halo, cyano, benzyl, or substituted aryl.

8. The process of claim 3 wherein R is $C_1$–$C_4$ alkyl, $R_1$ is —$OR_2$ or —$N(R_2)R_3$ and is in the 6-position; Q is phenyl, cyano, $C_1$–$C_4$ alkoxycarbonyl, $C_1$–$C_4$ alkanoyl, benzoyl, carbamoyl, N-$C_1$–$C_4$ alkylcarbamoyl, N-phenylcarbamoyl, $C_1$–$C_4$ alkylsulfonyl, phenylsulfonyl, or a heterocyclic aryl ring optionally substituted one or more times with $C_1$–$C_4$ alkyl, $C_1$–$C_4$ alkoxy, carboxy, $C_1$–$C_4$ alkoxycarbonyl, halo, cyano, benzyl, or substituted aryl.

* * * * *